United States Patent
Klade et al.

(10) Patent No.: US 12,343,381 B2
(45) Date of Patent: *Jul. 1, 2025

(54) DOSAGE REGIMEN FOR PEGYLATED INTERFERON

(71) Applicant: PharmaEssentia Corporation, Taipei (TW)

(72) Inventors: Christoph Klade, Vienna (AT); Oleh Zagrijtschuk, Vienna (AT); Ko-Chung Lin, Lexington, MA (US)

(73) Assignee: PHARMAESSENTIA CORPORATION, Taipei (TW)

(*) Notice: Subject to any disclaimer, the term of this patent is extended or adjusted under 35 U.S.C. 154(b) by 0 days.

This patent is subject to a terminal disclaimer.

(21) Appl. No.: 18/088,272

(22) Filed: Dec. 23, 2022

(65) Prior Publication Data

US 2023/0131552 A1 Apr. 27, 2023

Related U.S. Application Data

(63) Continuation of application No. 15/518,423, filed as application No. PCT/US2015/059410 on Nov. 6, 2015, now Pat. No. 11,559,567.

(30) Foreign Application Priority Data

Nov. 6, 2014 (EP) .................... 14192114

(51) Int. Cl.
- A61K 38/21 (2006.01)
- A61K 47/60 (2017.01)
- C07K 14/555 (2006.01)
- C07K 14/56 (2006.01)

(52) U.S. Cl.
CPC ............ A61K 38/212 (2013.01); A61K 38/21 (2013.01); A61K 47/60 (2017.08); C07K 14/555 (2013.01); C07K 14/56 (2013.01)

(58) Field of Classification Search
CPC .......... A61K 38/212; A61K 47/60; A61P 7/00
See application file for complete search history.

(56) References Cited

U.S. PATENT DOCUMENTS

| | | | |
|---|---|---|---|
| 5,382,657 A | 1/1995 | Karasiewicz et al. | |
| 5,643,575 A | 7/1997 | Martinez | |
| 5,738,846 A | 4/1998 | Greenwald et al. | |
| 5,824,784 A | 10/1998 | Kinstler | |
| 5,919,455 A | 7/1999 | Greenwald | |
| 5,932,462 A | 8/1999 | Harris | |
| 5,951,974 A | 9/1999 | Gilbert | |
| 6,824,768 B2 | 11/2004 | Stalgis | |
| 7,125,843 B2 | 10/2006 | DeFrees et al. | |
| 8,273,343 B2 | 9/2012 | Lin | |
| 8,617,532 B2 | 12/2013 | Lin et al. | |
| 2004/0136952 A1 | 7/2004 | Bhaskaran et al. | |
| 2005/0009988 A1 | 1/2005 | Harris | |
| 2005/0107277 A1 | 5/2005 | Lin et al. | |
| 2005/0143292 A1 | 6/2005 | DeFrees et al. | |
| 2006/0057070 A1 | 3/2006 | Assaly et al. | |
| 2006/0166932 A1 | 7/2006 | Zeldis | |
| 2009/0035273 A1 | 2/2009 | Liu | |
| 2009/0053177 A1 | 2/2009 | Lin | |
| 2011/0262380 A1 | 10/2011 | Lin | |
| 2012/0310140 A1 | 12/2012 | Kramer et al. | |

FOREIGN PATENT DOCUMENTS

| | | |
|---|---|---|
| CN | 1966547 A | 5/2007 |
| CN | 1970572 A | 5/2007 |
| CN | 101002944 A | 7/2007 |
| CN | 101104078 A | 1/2008 |
| CN | 101108895 A | 1/2008 |
| CN | 101491682 A | 7/2009 |
| CN | 101514229 A | 8/2009 |
| CN | 101671390 A | 3/2010 |
| EA | 2012/00865 A1 | 11/2012 |
| EP | 0809996 A2 | 12/1997 |
| EP | 0809996 A3 | 4/1999 |
| EP | 1834963 A1 | 9/2007 |
| EP | 1869079 A2 | 12/2007 |
| JP | 2003/513681 A | 4/2003 |
| JP | 2003/527090 A | 9/2003 |
| JP | 2005/525302 A | 8/2005 |
| JP | 2013513611 | 4/2013 |
| WO | WO 95/11924 A1 | 5/1995 |
| WO | WO 96/21469 A1 | 7/1996 |
| WO | WO 98/41562 | 9/1998 |
| WO | WO 03/044056 A2 | 5/2003 |
| WO | WO-2004/022630 A3 | 3/2004 |
| WO | WO-2005/000359 A2 | 1/2005 |
| WO | WO-2006/024953 A3 | 3/2006 |
| WO | WO 2006/084089 | 8/2006 |
| WO | WO-2006/094530 A1 | 9/2006 |
| WO | WO-2006/095029 A2 | 9/2006 |

(Continued)

OTHER PUBLICATIONS

Extended European Search Report dated Dec. 20, 2023, pp. 1-13.
Arnason "Long-Term Experience with Interferon Beta-1b (Betaferon®) in Multiple Sclerosis" Journal of Neurology vol. 252, pp. 28-33, 2005.
Bailon et al "Rational Design of a Potent, Long-Lasting Form of Interferon: A 40 kDa Branched Polyethylene Glycol-Conjugated Interferon α-2a for the Treatment of Hepatitis C" Bioconjugate Chemistry vol. 12, pp. 195-202, 2001.
Baker et al "N-Terminally PEGylated Human Interferon-β-1a with Improved Pharmacokinetic Properties and in Vivo Efficacy in a Melanoma Angiogenesis Model" Bioconjugate Chemistry vol. 17, pp. 179-188, 2006.

(Continued)

Primary Examiner — Xiaozhen Xie
(74) Attorney, Agent, or Firm — Singleton Law, PLLC; Chainey P. Singleton

(57) ABSTRACT

Described is a method for treating an infectious disease, cancer, or myeloproliferative disease in a subject, wherein a 50 to 540 μg dose of a pegylated type I interferon is administered to the subject at a regular interval for a treatment period, the interval being 3 to 8 weeks.

22 Claims, 2 Drawing Sheets

(56) References Cited

FOREIGN PATENT DOCUMENTS

| WO | WO 2009/023826 | 2/2009 |
|---|---|---|
| WO | WO-2009/030065 A1 | 3/2009 |
| WO | WO-2009/030066 A1 | 3/2009 |
| WO | 2010014874 A3 | 2/2010 |
| WO | WO-2010/014874 A2 | 2/2010 |
| WO | WO-2011/072138 A2 | 6/2011 |

OTHER PUBLICATIONS

Basu et al "Structure-Function Engineering of Interferon-β-1b for Improving Stability, Solubility, Potency, Immunogenicity, and Pharmacokinetic Properties by Site-Selective Mono-PEGylation" Bioconjugate Chemistry vol. 17, pp. 618-630, 2006.
Berendsen "A Glimpse of the Holy Grail?" Science vol. 282, pp. 642-643, 1998.
Bradley et al "Limits of Cooperativity in a Structurally Modular Protein: Response of the Notch Ankyrin Domain to Analogous Alanine Substitutions in Each Repeat" Journal of Molecular Biology vol. 324, pp. 373-386, 2002.
Barosi et al "JAK2$^{V617F}$ Allele Burden ≥50% is Associated with Response to Ruxolitinib in Persons with MPN-Associated Myelofibrosis and Splenomegaly Requiring Therapy" Leukemia accepted article preview, 2016.
Bjorn et al "Combination Therapy with Interferon and JAK1-2 Inhibitor is Feasible: Proof of Concept with Rapid Reduction in JAK2V617F-Allele Burden in Polycythemia Vera" Leukemia Research Reports vol. 3, pp. 73-75, 2014.
clinicaltrials.gov "History of Changes for Study: NCT02218047" pp. 1-6, retrieved Jun. 13, 2018.
dictionary.com "Mopiety" pp. 1-3, retrieved Mar. 12, 2010.
Deininger et al "The Effect of Long-Term Ruxolitinib Treatment on JAK2p. V617F Allele Burden in Patients with Myelofibrosis" Blood vol. 126, pp. 1551-1554, 2015.
European Medicines Agency "Public Summary of Opinion on Orphan Designation" pp. 1-4, Dec. 20, 2011.
Glisslinger et al "Ropeginterferon Alfa-2b, a Novel IFNα-2b, Induces High Response Rates with Low Toxicity in Patients with Polycythemia Vera" Blood vol. 126, pp. 1762-1769, 2015.
Gisslinger et al "Ropeginterferon Alfa-2b Versus Standard Therapy for Polycythaemia Vera (Proud-PV and Continuation-PV): A Randomised, Non-Inferiority, Phase 3 Trial and Its Extension Study" Lancet Haematology, 2020.
Gupta et al "A Phase 1/2, Open-Label Study Evaluating Twice-Daily Administration of Momelotinib in Myelofibrosis" Haematologica vol. 102, pp. 94-102, 2017.
Huang, et al. Ropeginterferon alfa-2b every 2 weeks as a novel pegylated interferon for patients with chronic hepatitis B. Hepatology International . Oct. 24, 2020. pp. 97-1008. vol. 14.
Hsu et al. Ropeginterferon Alfa-2b administered every two weeks for patients with genotype 2 chronic hepatitis C. Journal of the Formosan Medical Association. 2021. pp. 956-964. vol. 120.
Ianotto et al "Benefits and Pitfalls of Pegylated Interfern-α2a Therapy in Patients with Myeloproliferative Neoplasm-Associated Myelofibrosis: A French-Intergroup of Myeloproliferative Neoplasms (FIM) Study" Haematologica vol. 103, pp. 438-446, 2018.
Ianotto et al "PEG-IFN-α-2a Therapy in Patients with Myelofibrosis" British Journal of Haematology vol. 46, pp. 218-230, 2009.
Kiladjian et al "Interferon-Alpha for the Therapy of Myeloproliferative Neoplasms: Targeting the Malignant Clone" Leukemia accepted article preview, 2015.
Kiladjian et al "Thromboembolic Risk Reduction and High Rate of Complete Molecular Response with Long-Term Use of Ropeginterferon Alpha-2b in Polycythemia Vera: Results from a Randomized Controlled Study" Blood vol. 134, Supplement 1, 2019.
Kiladjian et al "High Molecular Response Rate of Polycythemia Vera Patients Treated with Pegylated Interferon α-2a" Blood vol. 108, pp. 2037-2040, 2006.
Kiladjian et al., "Pegylated interferon-alfa-2a induces complete hematologic and molecular responses with low toxicity in polycythemia vera", Blood, 112, pp. 3065-3072, Oct. 15, 2008.
Langer et al "Pegylated Interferon for the Treatment of High Risk Essential Thrombocythemia: Results of a Phase II Study" Haematologica vol. 90, pp. 1333-1338, 2005.
Li et al "Synthesis of Polyethylene Glycol (PEG) Derivatives and PEGylated-Peptide Biopolymer Conjugates" Biomacromolecules vol. 4, pp. 1055-1067, 2003.
Lin et al "Pharmaessentia Corp." The Ninth Annual BioAsia International Conference, Company Profiles.
Masarova et al "Efficacy and Safety of Pegylated Interferon Alpha-2a in Patients with Essential Thrombocythemia (ET) and Polycythemia Vera (PV): Results of a Phase 2 Study After a 7-Year Median Follow-Up" Lancet Haematology vol. 4, pp. e165-e175, 2017.
Mesa "Highlights in Myeloproliferative Neoplasms From the 60$^{th}$ American Society of Hematology Annual Meeting" Clinical Advances in Hematology and Oncology vol. 17, Supplemental 2, 2019.
Mickle, et al., "Genotype-phenotype relationships in cystic fibrosis", Medical Clinics of North America, vol. 84, No. 3, May 2000 pp. 597-607.
Ngo et al "Computational Complexity, Protein Structure Prediction, and the Levinthal Paradox" The Protein Folding Problem and Tertiary Structure Prediction, pp. 491-495, 1994.
Pai et al "Long-Acting Interferon for Myeloproliferative Neoplasms—An Update" Expert Review of Hematology vol. 9, pp. 915-917, 2016.
Proud-PV "Polycythemia Vera" pp. 1-2, retrieved Jun. 8, 2021.
Proud-PV "The Proud-PV Study" pp. 1-5, retrieved Jun. 8, 2021.
Quintas-Cardama, et al. "Pegylated Interferon Alfa-2a Yields High Rates of Hematologic and Molecular Response in Patients with Advanced Essential Thrombocythemia and Polycythemia Vera" Journal of Clinical Oncology, vol. 27, No. 32; Nov. 10, 2009.
Roberts, et al. "Chemistry for Peptide and Protein PEGylation" Advanced Drug Delivery Reviews; vol. 54; No. 4; XP-002293146; Jun. 17, 2002.
Rudinger "Characteristics of the Amino Acids as Components of a Peptide Hormone Sequence" Peptide Hormones, pp. 1-7, 1976.
Stahl et al "Management of Myelofibrosis: JAK Inhibition and Beyond" Expert Review of Hematology accepted article preview, 2017.
Sever et al "Therapeutic Options for Patients with Polycythemia Vera and Essential Thrombocythemia Refractory/Resistant to Hydroxyurea" Leukemia and Lymphoma Early Online, pp. 1-6, 2014.
Samuelsson et al "A Phase II Trial of Pegylated Interferon α-2b Therapy for Polycythemia Vera and Essential Thrombocythemia" Cancer vol. 106, pp. 2397-2405, 2006.
Schinzel et al "The Phosphate Recognition Site of *Escherichia coli* Maltodextrin Phosphorylase" Federation of European Biochemical Societies vol. 286, pp. 125-128, 1991.
Sigma Genosys "Designing Custom Peptides" pp. 1-2, retrieved Dec. 16, 2014.
Vannucchi et al "JAK2 Allele Burden in the Myeloproliferative Neoplasms: Effects on Phenotype, Prognosis and Change with Treatment" Therapeutic Advances in Hematology vol. 2, pp. 21-32, 2011.
Vannucchi et al "Ruxolitinib Reduces JAK2 p.V617F Allele Burden in Patients with Polycythemia Vera Enrolled in the Response Study" Annals of Hematology vol. 96, pp. 1113-1120, 2017.
Verger et al "Ropeginterferon Alpha-2b Targets JAK2V617F-Positive Polycythemia Vera Cells In Vitro and In Vivo" Blood Cancer Journal vol. 8, pp. 1-6, 2018.
Voet et al "Abnormal Hemoglobins" Biochemistry, pp. 235-241, 1995.
Webster et al "PEGylation of Somatropin (Recombinant Human Growth Hormone): Impact on Its Clearance in Humans" Xenobiotica vol. 38, pp. 1340-1351, 2008.
Zalipsky "Chemistry of Polyethylene Glycol Conjugates with Biologically Active Molecules" Advanced Drug Delivery Reviews vol. 16, pp. 157-182, 1995.

(56) References Cited

OTHER PUBLICATIONS

Zhang et al "Interferon Alpha 2b for Treating Patients with JAK2V617F Positive Polycythemia Vera and Essential Thrombocytosis" Asian Pacific Journal of Cancer Prevention vol. 15, pp. 1681-1684, 2014.

"AOP Orphan Pharmaceuticals Announces Progress of Pivotal Phase III Trial Proud-PV Of Novel Mono-Pegylated Interferon Alpha 2b for the Treatment Of Polycythemia Vera;" AOP Orphan; Jul. 10, 2013.

"AOP Orphan Pharmaceuticals Reports Positive Phase II Data of Novel Mono-Pegylated Interferon Alpha 2b for Treatment of Polycythemia Vera (PV);" AOP Orphan; Dec. 10, 2012.

"History of Changes for Study: NCT02218047", https://clinicaltrials.gov/ct2/history/NCT02218047?V1=View#StudyPageTop, Aug. 14, 2014; Retrieved on Dec. 22, 2021.

"Study Drugs—Proud-PV Phase III Study", http://web.archive.org/web/20140603131156/http://www.proud-pv.com/study-drugs.html, Jun. 3, 2014; Retrieved on Dec. 22, 2021.

Gissliner et al.; "Ropeginterferon alfa-2b versus standard therapy for polycythaemia vera (Proud-PV and Continuation-PV): a randomised, non-inferiority, phase 3 trial and its extension study", Lancet Haematol 2020; vol. 7, 7:e196-e208, Mar. 2020.

DOSAGE REGIMEN FOR PEGYLATED INTERFERON

CROSS-REFERENCE TO RELATED APPLICATIONS

This application is a continuation of U.S. Pat. No. 11,559,567, which has the U.S. patent Application Ser. No. 15/518,423, filed on Apr. 11, 2017, which is the National Stage of International Application No. PCT/US2015/059410, filed on Nov. 6, 2015, which claims priority to European Patent Application No. 14192114.8, filed on Nov. 6, 2014. The contents of all prior applications and patents are hereby incorporated by reference herein.

BACKGROUND

Interferons (IFNs) are proteins made and released by host cells in response to the presence of pathogens such as viruses, bacteria, parasites or tumor cells. In a typical scenario, a virus-infected cell will release interferons causing nearby cells to increase their anti-viral defenses.

IFNs belong to the large class of glycoproteins known as cytokines. Interferons are named for their ability to "interfere" with viral replication by protecting cells from virus infection. More than twenty distinct IFN genes and proteins have been identified in animals, including humans. They are typically divided among three classes: Type I IFN, Type II IFN, and Type III IFN. IFNs of all three classes are important for fighting viral infections and regulating the immune system.

Recombinant IFNs have been developed and are commercially available.

Due to their various biological activities, use of IFNs for treating a number of conditions, such as infectious diseases and cancers, has been proposed. However, use of IFNs has generally been limited by several shortcomings, including immunogenicity, which may lead to formation of neutralizing antibodies and loss of clinical response, and a short half-life, which means that frequent doses are required to maintain therapeutically effective concentrations of the protein.

These problems were partially solved by conjugating IFNs to polymers, such as polyethylene glycol. Several different types of IFN are now approved for use in humans, including a pegylated interferon-alpha-2b (Pegintron) and a pegylated interferon-alpha-2a (Pegasys). These pegylated drugs are injected once weekly, rather than two or three times per week, as is necessary for conventional interferon-alpha. When used with the antiviral drug ribavirin, pegylated interferon is effective for the treatment of hepatitis C.

However, while interferon-polymer conjugates are clinically beneficial, they also have a number of adverse side effects such as flu-like symptoms, increased body temperature, feeling ill, fatigue, headache, muscle pain, convulsion, dizziness, hair thinning, and depression. Erythema, pain and hardness on the spot of injection are also frequently observed.

Side effects are particularly important considerations when long term treatment is needed. Reducing the frequency of administration and total cumulative amount administered may decrease side effects and increase tolerability. However, previous such attempts did not show any satisfactory therapeutic effectiveness.

SUMMARY

In one aspect, described herein is a method of treating an infectious disease, cancer, or myeloproliferative disease in a subject, the method comprising administering to a subject in need thereof a 50 to 540 µg dose of a pegylated type I interferon at a regular interval of 2 to 4 weeks for a treatment period. (i.e., 3, 4, 5, 6, 7, or 8 weeks).

In one embodiment, the myeloproliferative disease is myelofibrosis, polycythemia vera, or essential thrombocythemia.

In another aspect, encompassed herein is a method of treating a myeloproliferative disease in a subject, the method comprising: administering to a subject in need thereof a 50 to 540 µg dose of a pegylated type I interferon at a first regular interval for a first treatment period, the first interval being 1 to 4 weeks, and administering to the subject a 50 to 540 µg dose of the pegylated type I interferon at a second regular interval for a second treatment period, the second interval being 3 to 8 weeks.

In one embodiment, the pegylated type I interferon is

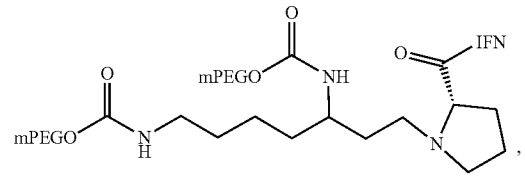

in which mPEG has a molecular weight of 20 kD and IFN is an interferon-$\alpha_{2b}$.

The total amount of the pegylated type I interferon administered to the subject per a given period during the second treatment period is lower than the total amount administered per the given period during the first treatment period.

In an embodiment, the first treatment period continues until the subject exhibits (i) normalization of at least one hematological parameter and/or (ii) at least 50% reduction of JAK2V617F allelic burden.

In one specific embodiment, the first interval is 1 to 2 weeks and the second interval is 4 weeks.

Also described herein is a pegylated type I interferon for use in treating an infectious disease, cancer, or myeloproliferative disease in a subject in need thereof, wherein a 50 to 540 µg dose of the pegylated type I interferon is administered to the subject at a regular interval for a treatment period, the interval being 3 to 8 weeks.

The details of one or more embodiments are set forth in the accompanying drawing and the description below. Other features, objects, and advantages of the embodiments will be apparent from the description and drawing, and from the claims.

DETAILED DESCRIPTION

Figure 1:
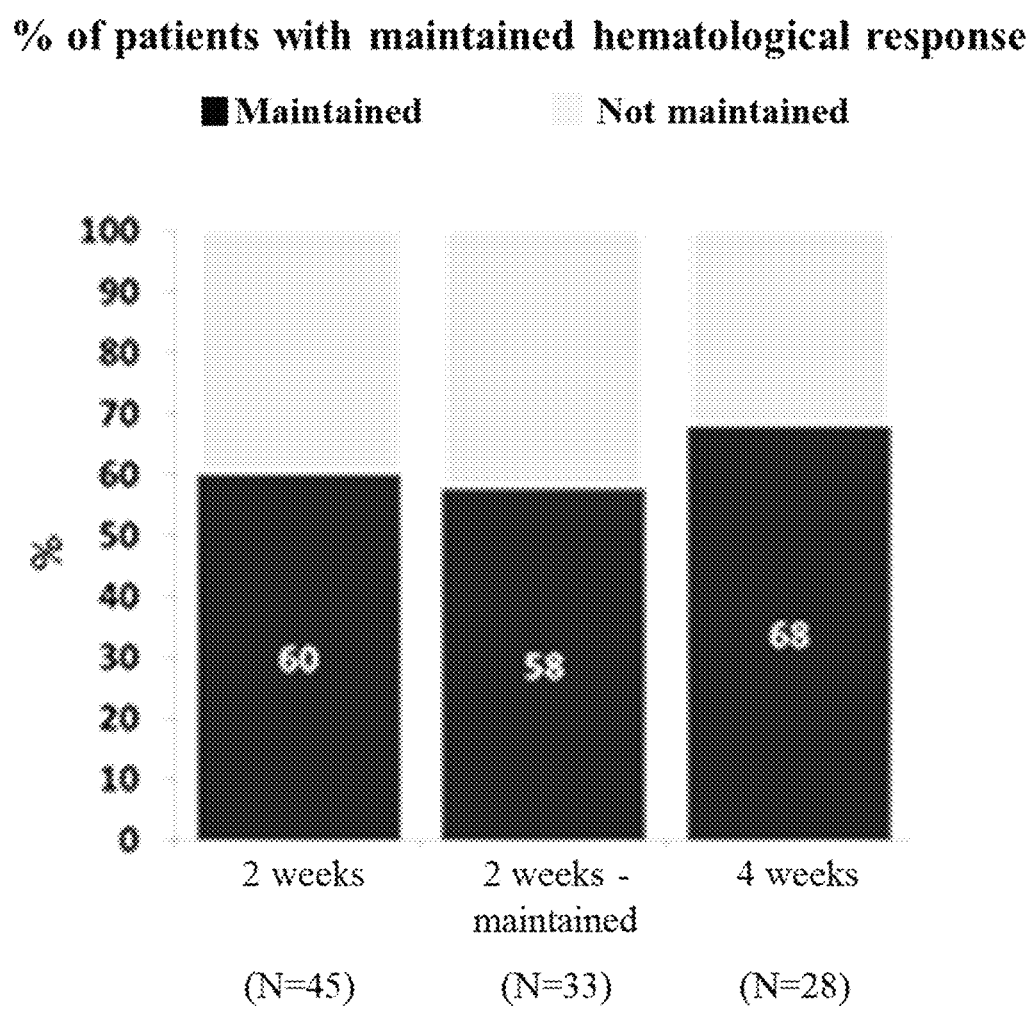
FIG. 1 is a bar graph showing maintenance of any hematological response before and after switch to a 4-week regimen.

Data described below demonstrated that, surprisingly, administration of a pegylated type I interferon at long intervals can provide efficient and even increased responses in subjects compared to a weekly or biweekly administration regimen. The reduced injection frequency also clearly and significantly improved tolerability and reduced adverse events. The data further showed that continuous administration of low doses of a pegylated interferon is an important variable for inducing molecular responses. It was also shown that the effects of long term administration of a pegylated type I interferon at low doses are pleiotropic, such as induction of immune-surveillance.

Accordingly, described herein are methods that involve administering a pegylated type I interferon at a regular interval to treat a subject in need thereof (e.g., a subject with an infectious disease, a cancer, or a myeloproliferative disease).

The pegylated type I interferon administered at a regular interval is selected from the group consisting of interferon-α, interferon-β, interferon-ω, interferon-λ and interferon-τ. More specifically, it is interferon-α 2b or 2a.

In a preferred embodiment, a pegylated interferon-α-2b is administered at a regular interval.

Lyophilized formulations containing a peg-interferon-α-2b, dibasic sodium phosphate anhydrous, monobasic sodium phosphate dihydrate, sucrose and polysorbate 80 are marketed by Schering Corporation, Kenilworth, NJ as PEGIntron® vials and PEG-Intron® Redipen (See PEG-Intron® Product Information, Rev. 2/05.). The Redipen® is a dual-chamber glass cartridge containing lyophilized PEGIntron in one chamber and sterile water for injection in the other chamber. The manufacturer recommends room temperature storage for PEG-Intron® vials (i.e., 25° C.), and refrigerated storage for PEG-Intron Redipen cartridges (i.e., 2° to 8° C.).

A pegylated interferon-α-2b made of human proteins is for example available under the trade name Pegasys®.

In one embodiment, a mono-pegylated, proline-substituted interferon-α-2b is administered at a regular interval.

The pegylated type I interferon can be a conjugate of formula I:

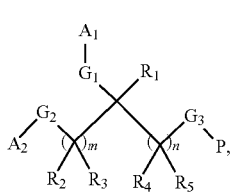

formula I wherein each of $R_1$, $R_2$, $R_3$, $R_4$, and $R_5$, independently, is H, $C_{1-5}$ alkyl, $C_{2-5}$ alkenyl, $C_{2-5}$ alkynyl, aryl, heteraryl, $C_{3-8}$ cycloalkyl, or $C_{3-8}$ heterocycloalkyl; each of $A_1$ and $A_2$, independently, is a polymer moiety; each of $G_1$, $G_2$, and $G_3$, independently, is a bond or a linking functional group; P is an interferon-α moiety; m is 0 or an integer of 1-10; and n is an integer of 1-10.

Referring to the above formula, the conjugate may have one or more of the following features: $G_3$ is a bond and P is interferon-α moiety in which the amino group at the N-terminus is attached to $G_3$; $A_1$ and $A_2$ are polyalkylene oxide moieties having a molecular weight of 2-100 kD (preferably 10-30 kD), each of $G_1$ and $G_2$ is

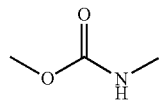

(in which O is attached to $A_1$ or $A_2$, and NH is attached to a carbon atom as shown in formula I), or each of $G_1$ and $G_2$ is urea, sulfonamide, or amide, (in which N is attached to a carbon atom as shown in formula I); m is 4, n is 2, and each of $R_1$, $R_2$, $R_3$, $R_4$, and $R_5$ is H; and the interferon-α moiety is a modified interferon-α moiety containing 1-4 additional amino acid residues.

In one embodiment, the conjugate is AOP2014/P1101, which has the formula:

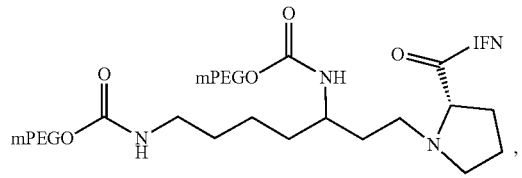

in which mPEG has a molecular weight of 20 kD and IFN is an interferon-am (e.g., a human interferon-$α_{2b}$).

The conjugate of formula I is described in detail in WO2009/023826A1. In particular, WO2009/023826A1 teaches a method of making AOP2014/P1101.

In any of the methods and uses described herein, the pegylated type I interferon can be administered by any means known in the art, e.g., via subcutaneous or intravenous route. The pegylated type I interferon can be formulated as an injectable formulation.

In one aspect, a pegylated type I interferon is administered to a subject in need thereof for a time period (i.e., a treatment period) at a dose of 50 to 540 μg at a regular interval, which is at least 3 weeks, e.g., at least 3, 4, 5, 6, 7, 8, or more weeks. For example, a dose can be administered every 3, 4, 5, 6, 7, or 8 weeks. An interval that is defined in days or months is also contemplated. A regular interval of 21 to 56 days (e.g., 21, 25, 26, 27, 28, 29, 30, 31, 35, 42, 49, and 56 days), one month, or two months can be utilized in the method.

The term "dose" refers to the amount of a compound administered to a subject at one time.

The term "interval" refers to the time between administration of two consecutive doses.

The treatment period can be at least 2, 3, 4, 5, 6, 7, 8, 9, 10, 11, 12, or more months. In one embodiment, the treatment period is 2, 3, or more years.

A dose administered during the treatment period ranges from 50 to 540 μg. The dose can be 50 μg, up to 55 μg, specifically up to 60 μg, specifically up to 65 μg, specifically up to 75 μg, specifically up to 80 μg, specifically up to 85 μg, specifically up to 90 μg, specifically up to 95 μg, specifically up to 100 μg, specifically up to 105 μg, specifically up to 110 μg, specifically up to 115 μg, specifically up to 120 μg, specifically up to 125 μg, specifically up to 130 μg, specifically up to 135 μg, specifically up to 140 μg, specifically up to 145 μg, specifically up to 150 μg, specifically up to 155 μg, specifically up to 160 μg, specifically up to 165 μg, specifically up to 170 μg, specifically up to 175 μg, specifically up to 180 μg, specifically up to 185 μg, specifically up to 190 μg, specifically up to 195 μg, specifically up to 200 μg, specifically up to 205 μg, specifically up to 210 μg, specifically up to 215 μg, specifically up to 225 μg, specifically up to 230 μg, specifically up to 235 μg, specifically up to 240 μg, specifically up to 245 μg, specifically up to 250 μg, specifically up to 255 μg, specifically up to 260 μg, specifically up to 265 μg, specifically up to 270 μg, specifically up to 275 μg. specifically up to 280 μg, specifically up to 285 µg, specifically up to 290 µg, specifically up to 295 µg, specifically up to 300 µg, specifically up to 305 µg, specifically up to 310 µg, specifically up to 315 µg, specifically up to 320 µg, specifically up to 325 µg, specifically up to 330 µg, specifically up to 335 µg, specifically up to 340 µg, specifically up to 345 µg, specifically up to 350 µg, specifically up to 400 µg, specifically up to 450 µg, specifically up to 500 µg, or up to 540 µg.

In an alternative embodiment, a dose administered during the treatment period is between 50 and 500 µg, specifically between 50 and 100 µg, alternatively between 100 and 150 µg, alternatively between 150 and 200 µg, alternatively between 200 and 250 µg, alternatively between 250 and 300 µg, alternatively between 300 and 350 µg, alternatively between 350 and 400 µg, alternatively between 400 and 450 µg, alternatively between 450 and 500 µg, or between 500 and 540 µg.

During any treatment period, the pegylated type I interferon can be administered at a constant dose, meaning that the same dose is administered each time or only minimally different doses are administered (e.g., dose variation or deviation of less than 10%, specifically less than 5%, specifically less than 1%). Alternatively, different doses can be administered at a regular interval during a treatment period. For example, the interferon can be administered at a particular dose at a regular interval for a certain time and it can then be administered at a different dose (higher or lower than the first dose) at the same regular interval.

The subject can be a subject who has not been treated with an interferon before or a subject who had previously been administered a dose (e.g., 12.5, 15, 18.75, or 25 µg) of a type I interferon once per week or every two weeks.

Administration of the pegylated type I interferon at a regular interval can be used to treat a myeloproliferative disease (MPD) selected from myeloproliferative neoplasms (MPN), specifically from chronic myelogenous leukemia, BCR-ABL1-positive, chronic neutrophilic leukemia, polycythemia vera, primary myelofibrosis, essential thrombocythemia, chronic eosinophilic leukemia not otherwise specified, mastocytosis, myeloproliferative neoplasms unclassifiable; myeloid and lymphoid neoplasms associated with eosinophilia and abnormalities of PDGFRA, PDGFRB or FGFR1, specifically myeloid and lymphoid neoplasms associated with PDGFRA rearrangement, myeloid neoplasms associated with PDGFRB rearrangement, myeloid and lymphoid neoplasms associated with FGFR1 abnormalities; myelodysplastic/myeloproliferative neoplasms (MDS/MPN), specifically chronic myelomonocytic leukemia, atypical chronic myeloid leukemia, BCR-ABL1-negative, juvenile myelomonocytic leukemia, provisional entity: refractory anemia with ring sideroblasts and thrombocytosis; myelodysplastic syndrome (MDS), specifically refractory cytopenia with unilineage dysplasia, refractory anemia, refractory neutropenia, refractory thrombocytopenia, refractory anemia with ring sideroblasts, refractory cytopenia with multilineage dysplasia, refractory anemia with excess blasts, myelodysplastic syndrome with isolated del(5q), myelodysplastic syndrome, unclassifiable, childhood myelodysplastic syndrome; acute myeloid leukemia and related neoplasms, specifically acute myeloid leukemia with recurrent genetic abnormalities, AML with t(8;21)(q22;q22); RUNX1-RUNX1T1, AML with inv(16)(p13.1q22) or t(16;16)(p13.1;q22); CBFB-MYH11, APL with t(15;17)(q22;q12); PML-RARA, AML with t(9;11)(p22;q23); MLLT3-MLL, AML with t(6;9)(p23;q34); DEKNUP214, AML with inv(3)(q21q26.2) or t(3;3)(q21;q26.2); RPN1-EVI1, AML (megakaryoblastic) with t(1;22)(p13;q13); RBM15-MKL1, acute myeloid leukemia with myelodysplasia-related changes, therapy-related myeloid neoplasms, acute myeloid leukemia, not otherwise specified, AML with minimal differentiation, AML without maturation, AML with maturation, acute myelomonocytic leukemia, acute monoblastic/monocytic leukemia, acute erythroid leukemia, pure erythroid leukemia, erythroleukemia, erythroid/myeloid, acute megakaryoblastic leukemia, acute basophilic leukemia, acute panmyelosis with myelofibrosis, myeloid sarcoma, myeloid proliferations related to Down syndrome, transient abnormal myelopoiesis, myeloid leukemia associated with Down syndrome, blastic plasmacytoid dendritic cell neoplasm; acute leukemias of ambiguous lineage, specifically acute undifferentiated leukemia, mixed phenotype acute leukemia with t(9;22)(q34;q11.2); BCR-ABL1, mixed phenotype acute leukemia with t(v;11q23); MLL rearranged, mixed phenotype acute leukemia, B-myeloid, NOS, mixed phenotype acute leukemia, T-myeloid, NOS, B lymphoblastic leukemia/lymphoma, specifically B lymphoblastic leukemia/lymphoma, NOS, B lymphoblastic leukemia/lymphoma with recurrent genetic abnormalities, B lymphoblastic leukemia/lymphoma with t(9;22)(q34;q11.2); BCR-ABL 1, B lymphoblastic leukemia/lymphoma with t(v;11q23); MLL rearranged, B lymphoblastic leukemia/lymphoma with t(12;21)(p13;q22) TEL-AML1 (ETV6-RUNX1), B lymphoblastic leukemia/lymphoma with hyperdiploidy, B lymphoblastic leukemia/lymphoma with hypodiploidy, B lymphoblastic leukemia/lymphoma with t(5;14)(q31;q32) IL3-IGH, B lymphoblastic leukemia/lymphoma with t(1;19)(q23;p13.3); TCF3-PBX1.

In one embodiment, the subject has a myeloproliferative disease such as myelofibrosis, polycythemia vera, or essential thrombocythaemia.

A subject in need thereof can be treated with a pegylated type I interferon using one dosage regimen for a time period and then switched to a different dosage regimen.

More specifically, a 50 to 540 µg dose of a pegylated type I interferon is administered to a subject in need thereof at a first regular interval for a first treatment period, the first interval being 1 to 4 weeks (e.g., 1, 2, 3, or 4 weeks), and subsequently, a 50 to 540 µg dose of the pegylated type I interferon is administered to the subject at a second regular interval for a second treatment period, the second interval being at least 3 weeks (e.g., 3, 4, 5, 6, 7, or 8 weeks).

Subjects who show a good response to a pegylated type I interferon dosage regimen can be switched to another regimen in which the interferon is administered at a lower dose or at a longer interval or both.

In one embodiment, the total amount of the pegylated type I interferon administered to the subject per a given period (e.g., 1 week, 2 weeks, 4 weeks, 1 month, or 2 months) during the second treatment period is lower (e.g., lower by 20%, 30%, 40%, 45%, 50%, or more) than the total amount administered per the same given period during the first treatment period. For example, the monthly total amount of the interferon administered during the second treatment period can be lower (e.g., 20%, 30%, 40%, 45%, 50%, or more lower) than the monthly total amount administered during the first treatment period.

The dose administered during the first treatment period and the dose administered during the second treatment period can be the same but at different intervals. Alternatively, the dose administered during the second treatment period can be lower than the dose administered during the first treatment period.

The first treatment period and the second treatment period can separately be at least 2, 3, 4, 5, 6, 7, 8, 9, 10, 11, 12, or more months (e.g., 2, 3, or more years).

The first treatment period can continue until the subject shows a good response to the treatment. Whether a subject is responding well to the treatment can be determined by a practitioner skilled in the art based on art-accepted criteria.

In one embodiment, the subject is switched to a second treatment regimen when he or she exhibits (i) normalization of at least one hematological parameter and/or (ii) at least 50% reduction of JAK2V617F allelic burden.

Specifically, a further decrease of the JAK2V617F allelic burden can be achieved due to switch to the second treatment regimen wherein the treatment interval is 3 to 8 weeks. More specifically, said reduction of the JAK2V617F allelic burden can be 60%, 65%, 70%, 75%, 80%, 85%, 90%, 95%, or up to 99%, specifically within a treatment period of 1, 2 or more years.

A hematological parameter is "normalized" when its value is deemed sufficient to alleviate a disease-associated adverse event (e.g., thrombosis or anemia) or reduce the risk thereof in the subject. Hematocrit, white blood cell count, and platelet counts are exemplary hematological parameters. Hematocrit of less than 45% (without phlebotomy in the previous two months), a platelet count of less than $400 \times 10^9/L$ and a white blood cell count of less than $10 \times 10^9/L$ may each be considered as a normalized hematological parameter.

Other indications of a good response can include a normal spleen size (measured via ultrasound), absence of any thromboembolic events, and a reduction of phlebotomy requirements by at least 50%.

If a subject continues to show a good response under the second treatment regimen, the subject may be switched to yet another regimen that further reduces the administration frequency or dose (or both) of the pegylated type I interferon.

The specific example below is to be construed as merely illustrative, and not limitative of the remainder of the disclosure in any way whatsoever. Without further elaboration, it is believed that one skilled in the art can, based on the description herein, utilize the present disclosure to its fullest extent. All publications cited herein are hereby incorporated by reference in their entirety.

Example 1

AOP2014/P1101 is a next generation long-acting pegylated IFN-α-2b, consisting predominantly of only one isoform, as opposed to other commercially available pegylated interferons.

Study Design

A phase I/II single arm dose escalation study with cohort extension included 51 patients with PV who could be either cytoreduction therapy naive or pretreated. AOP2014/P1101 was administered subcutaneously in a dose range of 50-540 μg every two weeks. Main objectives were to define the maximum tolerated dose as well as observe the long term safety and efficacy in terms of normalization of blood parameters and molecular abnormalities.

The option to switch to an "once every four weeks" schedule was implemented by the amended protocol for patients who responded well to the treatment and participated in the study for longer than one year. The dose of the study drug had to remain unchanged after the switch, resulting in a decrease (by approximately half) of the overall exposure to the drug. Outcomes of this switch are presented here.

Results

Patients were dosed every two weeks based on the Phase II dosing rules (period A—median exposure duration of 34 weeks and mean monthly dose of 484 μg) prior to the switch option. 33 patients were dosed every two weeks beyond the first year (period B—median exposure duration of 12 weeks and mean monthly dose of 413 μg), and showing benefit from treatment, were assessed as eligible for switch. 28 patients were then switched to a once every four weeks schedule (period C—median exposure duration of 42 weeks and mean monthly dose of 221 μg). Nine patients were each at a dose of 100 μg or less after the switch. Baseline characteristics of the included patients are shown in Table 1.

After the switch, blood parameters were normalized and remained stable following one year of treatment and could be maintained (hematocrit, median,%—period A: 43, period B: 43, period C: 42; WBC, median, G/l—period A: 6.1, period B: 5.9, period C: 5.7; platelets, median, G/l—period A: 246, period B: 211, period C: 204), Spleen length stayed stable within the normal range following the switch in the majority of patients either (mean, in cm—period A: 11.4, period B: 8.3, period C: 10.3).

TABLE 1

Baseline information

| Parameter | Value |
|---|---|
| Safety population, patients (all treated) | 51 |
| Age at study entry, years, median (min-max) | 56 (35-82) |
| Male, n (%) | 31 (61%) |
| Splenomegaly (length >12 cm on sonography), patients (%) | 31 (61%) |
| Spleen length on sonography, median in cm (min-max) | 13.1 (8.0-22.0) |
| Patients with phlebotomies in 3 months prior screening, n (%) | 31 (61%) |
| Number of phlebotomies in 3 months prior screening, median (range) | 2 (1-8) |
| PV history prior entry, months, median (Q1-Q3) | 17.0 (3.6-68.8) |
| Major cardiovascular events in the med. history, patients (%) | 11 (22%) |
| HU pre-treated, patients (%) | 17 (33%) |
| Hct, %, median (min-max) | 44.8 (36.9-53.8) |
| Platelets, G/L, median (min-max) | 429 (148-1016) |
| WBC, G/L, median (min-max) | 11.1 (4.7-30.9) |
| JAK2V617F-positive | 100% |
| % V617F allelic burden, median (min-max) | 41% (2%-100%) |
| Safety population, patients | 51 |
| Enrolled in Phase I | 25 |
| Enrolled in Phase II | 26 |
| Follow-up duration, weeks, median (min-max) | 80 (4-170) |
| Evaluable patients with treatment duration >1 year | 30 |
| Arms analyzed for the current comparison | |
| Period A, 2-weeks regimen: all patients excluding those who discontinued before week 18 (V5) | 45 |
| Period B, 2-weeks regimen - MAINTAINED for the purpose: completed the one year of treatment and became eligible for switched but were not switched for certain duration. | 33 |
| Period C, 4-weeks regimen: all patients who were switched to 4 week schedule. | 28 |

Note:
same patient may count twice within the contributing periods if not switched immediately but remained in a 2-week schedule beyond the first year and was switched to a 4-week schedule later on.

Complete response as best individual response could be maintained in 42% of the patients from period A, 55% from period B, and 67% from period C, while for the partial hematological responders the results were 60%, 71% and 67%, respectively. Molecular response improved continuously over time, being maintained at the best individual level in 31% of the period A patients, compared to 42% of the period B patients and 75% of the period C patients. The decrease of application frequency and total dose exposure led to a decrease of the occurrence of all drug related adverse events from 0.17/0.09 (period A) and 0.3/0.09 (period B) to 0.08/0.03 (period C) (measured as mean count of adverse events [AE] per patient week exposure).

The maintenance of any hematological response before and after the switch to the 4-week regime is shown in FIG. 1 and Table 2.

TABLE 2

Maintenance of any hematological response between three comparison arms

| 4 weeks vs. 2 weeks | | 2 weeks | | |
|---|---|---|---|---|
| p (McNemar) = 0.782 | | Not maintained | Maintained | Total |
| 4 weeks | Not maintained | 3<br>10.7% | 6<br>21.4% | 9<br>32.1% |
| | Maintained | 7<br>25.0% | 12<br>42.9% | 19<br>67.9% |
| | Total | 10<br>35.7% | 18<br>64.3% | 23<br>100.0% |
| 4 weeks vs. 2 weeks-MAINT. | | 2 weeks-MAINTAINED | | |
| p (McNemar) = 0.564 | | Not maintained | Maintained | Total |
| 4 weeks | Not maintained | 3<br>11.5% | 5<br>19.2% | 8<br>30.8% |
| | Maintained | 7<br>26.9% | 11<br>42.3% | 18<br>69.2% |
| | Total | 10<br>38.5% | 16<br>61.5% | 26<br>100.0% |

Figure 2:
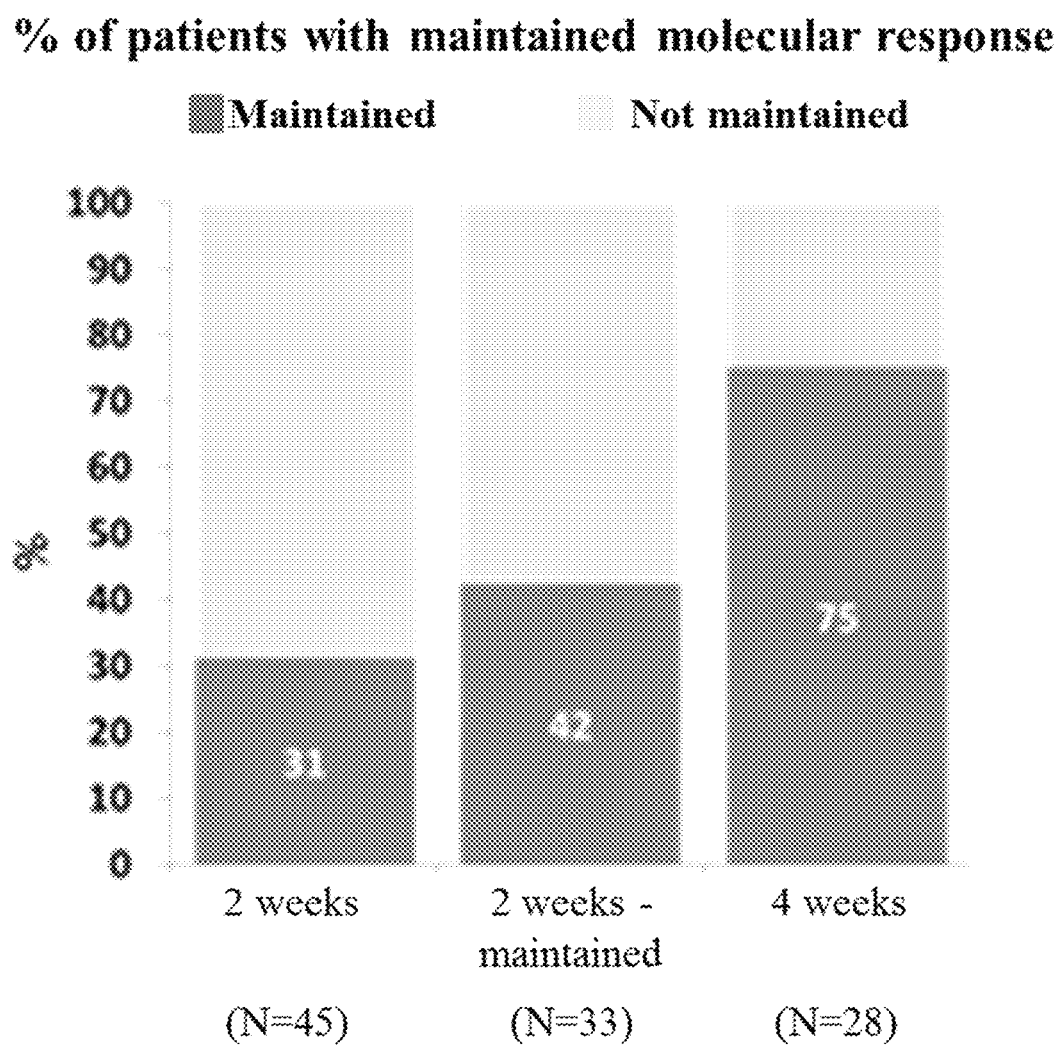
FIG. 2 is a bar graph showing maintenance of any molecular response before and after switch to 4-week regimen.

The maintenance of any molecular response before and after the switch to the 4-week regimen is shown in FIG. 2 and Table 3.

TABLE 3

Maintenance of any molecular response between three comparison arms

| 4 weeks vs. 2 weeks | | 2 weeks | | |
|---|---|---|---|---|
| p (McNemar) = 0.020 | | Not maintained | Maintained | Total |
| 4 weeks | Not maintained | 4<br>14.3% | 3<br>10.7% | 7<br>25.0% |
| | Maintained | 12<br>42.9% | 9<br>32.1% | 21<br>75.0% |
| | Total | 16<br>57.1% | 12<br>42.9% | 28<br>100.0% |
| 4 weeks vs. 2 weeks-MAINT. | | 2 weeks-MAINTAINED | | |
| p (McNemar) = 0.052 | | Not maintained | Maintained | Total |
| 4 weeks | Not maintained | 4<br>15.4% | 3<br>11.5% | 7<br>26.9% |
| | Maintained | 10<br>38.5% | 9<br>34.0% | 19<br>73.1% |
| | Total | 14<br>53.8% | 12<br>46.2% | 26<br>100.0% |

The data from endpoints pre-defined in the prospective study demonstrated that the feasibility of further reducing the frequency of AOP2014/P1101 administration to once every four weeks in responding patients, previously treated every two weeks. The reduced injection frequency was not associated with a lack of response, but clearly improved tolerability. Finally, the continuous reduction of the JAK2 allelic burden in the subjects indicated that duration of interferon exposure, rather than dose, is important for inducing molecular responses. The findings described above suggest that interferon-α-associated effects in PV are pleiotropic (e.g., induction of immune-surveillance), which can be continuously maintained at lower AOP2014/P1101 levels.

Example 2

A phase I/II single arm dose escalation study with cohort extension includes at least 30 patients with essential thrombocythemia who could be either undergo cytoreduction therapy naive or pretreated. AOP2014/P1101 is administered subcutaneously in a dose range of 50-540 μg every two weeks. The maximum tolerated dose as well as the long term safety and efficacy in terms of normalization of blood parameters and molecular abnormalities are observed.

The option to switch to an "once every four weeks" schedule is implemented for patients who respond well to the treatment and participate in the study for longer than one year. Patients who are dosed every two weeks beyond the first year and showing benefit from treatment are assessed as eligible for switch. The patients are then switched to a once every four weeks schedule. The dose of the study drug shall remain unchanged after the switch, resulting in a decrease (by approximately half) of the overall exposure to the drug.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the described embodiments, and without departing from the spirit and scope thereof, can make various changes and modifications of the embodiments to adapt it to various usages and conditions. Thus, other embodiments are also within the claims.

What is claimed is:

1. A method of treating a myeloproliferative disease in a subject, wherein the myeloproliferative disease is polycythemia vera, the method comprising:
   administering to a subject in need thereof a 50 to 540 μg dose of a pegylated type I interferon which has the following structure:

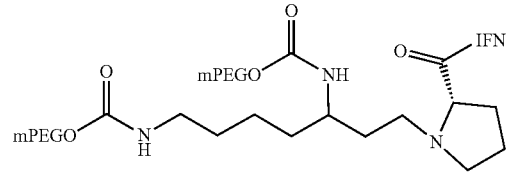

wherein the IFN is an interferon-$α_{2b}$, and each of the mPEG has a molecular weight of 20 kD; and wherein the pegylated type I interferon is administered at an interval of every 2 to 4 weeks for a treatment period, and wherein the treatment period is at least 16 months.

2. The method of claim 1, wherein the interval is every 2 weeks.

3. The method of claim 1, wherein the interval is every 4 weeks.

4. The method of claim 1, wherein a constant dose of the pegylated type I interferon is administered during the treatment period.

5. The method of claim 1, wherein the dose of the pegylated type I interferon comprising a different dosage administration during the treatment period.

6. The method of claim 1, wherein the subject had previously received an initial treatment for an initial treatment period comprising administering a dose of the pegylated type I interferon once per week for 12 months, 14 months, or 15 months.

7. The method of claim 6, wherein a constant dose of the pegylated type I interferon is administered during the initial treatment period.

8. The method of claim 7, wherein a constant dose is administered during the treatment period, which is lower than the constant dose administered during the initial treatment period.

9. The method of claim 7, wherein a constant dose is administered during the treatment period, which is the same constant dose as administered during the initial treatment period.

10. The method of claim 6, wherein a different dose of the pegylated type I interferon is administered during the initial treatment period.

11. The method of claim 6, wherein the total amount of the pegylated type I interferon administered to the subject per a given period during the treatment period is lower than the total amount administered per the given period during the initial treatment period.

12. The method of claim 1, wherein the subject exhibits
(i) normalization of at least one hematological parameter, and/or
(ii) at least 50% reduction of JAK2V617F allelic burden.

13. The method of claim 12, wherein the at least one hematological parameter is hematocrit, white blood cell count (WBC), or platelet count.

14. The method of claim 13, wherein the hematocrit is less than 45%, the WBC is less than or equal to $10\times10^9$/L, and the platelet count is less than or equal to $400\times10^9$/L.

15. A method of treating a myeloproliferative disease in a subject, wherein the myeloproliferative disease is polycythemia vera, the method comprising:
(i) administering, for a first treatment period, to a subject in need thereof a 50 to 540 μg dose of a pegylated type I interferon at a first interval of every 1 to 4 weeks, wherein the first treatment period is at least 12 months, at least 14 months, at least 15 months, or at least 16 months; and
(ii) administering, for a second treatment period, to the subject a 50 to 540 μg dose of the pegylated type I interferon at a second interval of every 3 to 4 weeks, wherein the second treatment period begins after the first treatment period,
wherein the pegylated type I interferon has the following structure:

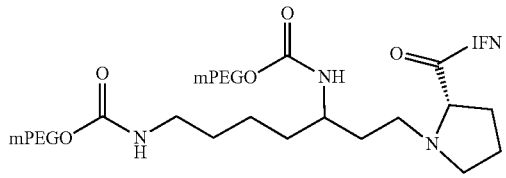

wherein the IFN is an interferon-$\alpha_{2b}$, and each of the mPEG has a molecular weight of 20 kD.

16. The method of claim 15, wherein the first regular interval is 1 to 2 weeks.

17. The method of claim 15, wherein the second regular interval is 4 weeks.

18. The method of claim 15, wherein the first treatment period is 14 months or 15 months.

19. The method of claim 15, wherein the second treatment period is at least 3 weeks to 12 months, or longer than 12 months.

20. The method of claim 15, wherein the first treatment period continues until the subject exhibits: (i) normalization of at least one hematological parameter; and/or (ii) at least 50% reduction of JAK2V617F allelic burden.

21. The method of claim 20, wherein the at least one hematological parameter is hematocrit, white blood cell count (WBC), or platelet count.

22. The method of claim 21, wherein the hematocrit is less than 45%, the WBC is less than or equal to $10\times10^9$/L, and the platelet count is less than or equal to $400\times10^9$/L.

* * * * *